United States Patent
Boufendi et al.

(10) Patent No.: US 8,689,652 B2
(45) Date of Patent: Apr. 8, 2014

(54) METHOD FOR DETERMINING THE SURFACE RADIUS AND/OR PARTICLE DENSITY OF A POWDER

(75) Inventors: Laïfa Boufendi, Saint Denis en Val (FR); Gaëtan Wattieaux, Orléans (FR)

(73) Assignees: Centre National de la Recherche Scientifique, Paris (FR); Universite d'Orleans, Orleans (FR)

( * ) Notice: Subject to any disclaimer, the term of this patent is extended or adjusted under 35 U.S.C. 154(b) by 351 days.

(21) Appl. No.: 13/257,104

(22) PCT Filed: Mar. 12, 2010

(86) PCT No.: PCT/FR2010/000207
§ 371 (c)(1),
(2), (4) Date: Oct. 6, 2011

(87) PCT Pub. No.: WO2010/106240
PCT Pub. Date: Sep. 23, 2010

(65) Prior Publication Data
US 2012/0137796 A1     Jun. 7, 2012

(30) Foreign Application Priority Data
Mar. 17, 2009 (FR) ...................................... 09 01240

(51) Int. Cl.
*G01N 15/00* (2006.01)

(52) U.S. Cl.
USPC ........................................................ 73/865.5

(58) Field of Classification Search
USPC ........................................................ 73/865.5
See application file for complete search history.

(56) References Cited

U.S. PATENT DOCUMENTS 5,214,386 A * 5/1993 Singer et al. .................. 324/452
6,553,849 B1 * 4/2003 Scofield et al. ............... 73/865.5

FOREIGN PATENT DOCUMENTS

WO    WO 00/25109 A1    5/2000

OTHER PUBLICATIONS

International Search Report and Written Opinion for Application No. PCT/FR2010/000207 (undated ).

Boufendi, L. et al., *Detection of Particles of Less Than 5 nm in Diameter Formed in an Argon-Silane Capacitively Radio-Frequency Discharge*, Applied Physics Letters, vol. 79, No. 26 (2001), pp. 4301-4303.

Kawamura, E. et al., *Ion Energy Distributions in rf Sheaths; Review, Analysis and Simulation*, Plasma Sources Sci. Technol. 8 (1999), pp. R45-R64.

* cited by examiner

*Primary Examiner* — Hezron E Williams
*Assistant Examiner* — Nathaniel Kolb
(74) *Attorney, Agent, or Firm* — Alston & Bird LLP

(57) ABSTRACT

This invention relates to a method for determining the average surface radius ro and/or the density r of the particles of a nanopowder in a sample levitating in an electropositive plasma with a volume V formed between a first electrode powered by a radiofrequency voltage and a second electrode with a fixed voltage, in particular a ground one, characterized in that: V is the amplitude at the measuring time t of the radiofrequency voltage RF powering the first electrode when the powder is present in the plasma, V is the amplitude of said radiofrequency voltage powering the first electrode in the absence of powder in the plasma, V is the self-polarization voltage of the first electrode at the time t when the powder is present in the plasma, V is the self-polarization voltage of the first electrode in the absence of powder in the plasma, $\Delta A_B$ is the surface variation of the second electrode in the presence of powder at the time t relative to a situation in which powder is absent, and the values of n and K are determined by means of calibrating by tracing a curve in which ro is a function of $\Delta A_B$ and of $V_{RF}$ from experimental data obtained from powders having a known particle diameter by measuring $V_{RF}$, $V_{RF(O)}$, $V_{DC}$, and $V_{DC(0)}$ and by applying a regression to said curve.

$$n_D = \frac{1}{4\pi K^2 V \Delta A_B} \times \left(\frac{1}{V_{RF}} - \frac{1}{V_{RF(0)}}\right)^{2n}$$

$$r_D = K \frac{\Delta A_B}{\left(\frac{1}{V_{RF}} - \frac{1}{V_{RF(0)}}\right)^n}$$

$$\underset{AA}{Avec} : K = \frac{\varepsilon_0 C}{q\, V\, D^n}, \Delta A_B = \frac{\frac{\delta(t)}{\delta(0)} - 1}{\frac{1}{A_{M0}} + \frac{1}{A_{B0}}},$$

-continued $$\delta(t) = \frac{\pi}{\arccos\left(\frac{V_{DC}}{V_{RF}}\right)} - 1$$

$$\underset{BB}{et}\ \delta(0) = \frac{\pi}{\arccos\left(\frac{V_{DC(0)}}{V_{RF(0)}}\right)} - 1$$

*AA* with

*BB* and

10 Claims, 7 Drawing Sheets

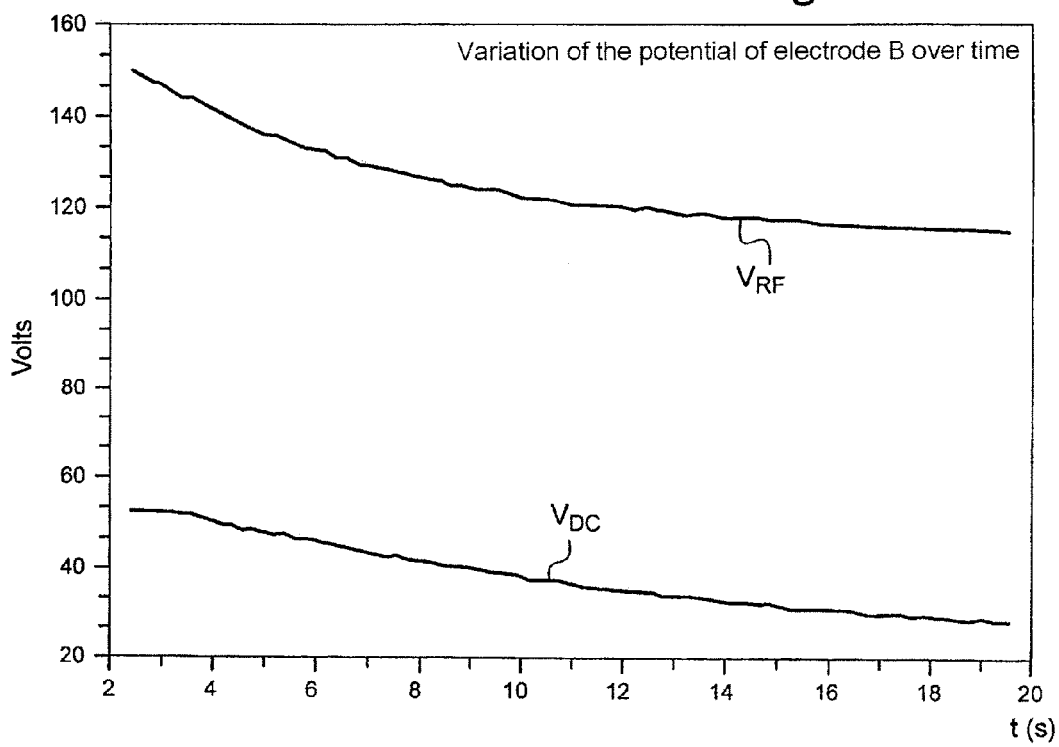
Fig.4
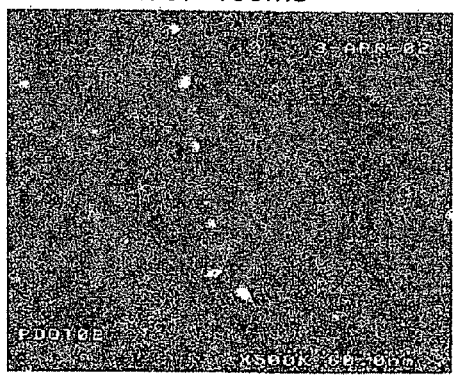
Fig.5
10W. t1=100ms
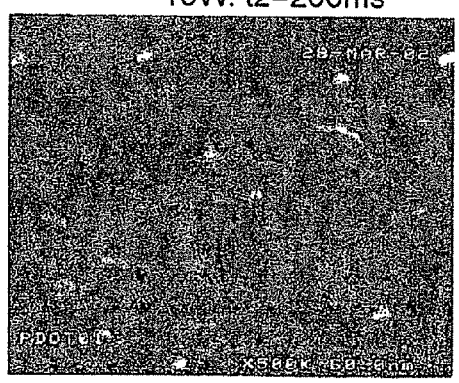
10W. t2=200ms

METHOD FOR DETERMINING THE SURFACE RADIUS AND/OR PARTICLE DENSITY OF A POWDER

FIELD OF THE INVENTION

The present invention relates to determining the mean surface radius $r_D$ and/or the density $n_D$ of particles of a powder, in particular a nanopowder in a plasma of volume V formed between a first electrode fed with a radiofrequency (RF) voltage and a second electrode taken to a constant voltage, in particular ground voltage.

BACKGROUND OF THE INVENTION

Developments concerning applications of nanomaterials are continuously increasing. The reports of scientific commissions (for example such as the AFSSET 2006 report in France entitled "Rapport AFSSET—les nanomatériaux: effets sur la santé de l'homme et sur l'environnement—juillet 2006" [AFSETT report—Nanomaterials: effects on human health and on the environment—July 2006]) show that in the next ten years the economy will be strongly affected by the production of nanomaterials, given that they involve numerous socioeconomic domains such as energy, materials for energy, medicine, electronics, cosmetics, and composite materials, to mention only a few examples. These nanomaterials are going to appear in a great variety of forms that depend closely on the technologies concerned. According to M. C. Roco [M. C. Roco, "International perspective on government nanotechnology funding in 2005", J. Nanopart. Res. 7(6), pp. 707-712, 2005], they may be classified into four major domains, as follows:

1) passive nanostructures involving both dispersed and agglomerated nanostructures (aerosols, colloids) and materials incorporating nanostructures (coatings, nanoparticle reinforcement of composites, nanostructured metals, polymers, ceramics, etc. . . . );

2) active nanostructures that comprise those that are bioactive and that have medical (or health) effects (molecules that are carried and taken to identified targets, biodevices, . . . ) and those that have physicochemical activity (three-dimensional transistors, amplifiers, actuators, adaptive structures, . . . );

3) nanosystems such as guided assemblies, three-dimensional networks, and hierarchical architectures, robotics, . . . ; and 4) molecular nanosystems relating to molecular and atomic devices, emerging functions, . . . .

The present growth of such nanomaterials in all fields of human activity leads legitimately to questions being raised on the health and environmental consequences. In a recent article in the journal "Technology Review" [www.technologyreview.fr/nano-tech/?id=196], mention is made of health problems associated with everyday use of compositions (e.g. household cleaners) even though goods of this type have doubtless obtained all of the health authorizations that are presently required before being launched on the market. Similarly, carbon nanoparticles have been accused of being responsible for pathology of the optic nerve in mice [G. Oberdörster, E. Oberdörster, J. Oberdörster, "Concepts of nanoparticle dose metric and response metric", in Environ Health Perspect. 2007, June, 115(6):A290]—(G. Oberdörster, University of Rochester). Other studies have revealed problems associated with the presence of fullerenes (E. Oberdörster, Duke University) or of carbon nanotubes [Chuff-Wing Lam, John T. James, Richard McCluskey, and Robert L. Hunter, Toxicological Sciences 77, pp. 126-134 (2004)] (C. W. Lam, NASA, Houston). Other substances are regularly being added to the list. That has naturally drawn attention to the validity of the criteria used for validating products and their individual ingredients. At present, a case-by-case rule is used since there is no methodology that is adapted to validating nanomaterials, thereby raising a fundamental problem.

Furthermore, the appearance of nanoparticles in the plasmas used in the fabrication methods of microelectronic industries lead to irremediable defects in the devices being made. The reject rate may exceed 50% in certain sectors. That situation also applies to white rooms, i.e. to the immediate environment of machines, and also of operators, where the measurement systems are capable of measuring powders in suspension in air providing powder size is greater than or equal to 0.5 micrometers ($\mu$m). Thus, needs in terms of in situ detection and measurement in gas are of great importance.

Most of the methods implemented at present are based on the interaction between a light beam and powders. They can be found in a variety of versions for in situ measurements such as light scattering (including lidars) and laser-induced incandescence. Other versions require samples to be collected and put into suspension in an aqueous solution in order to perform ex situ measurements. For all methods enabling characterization to be performed in situ, it is necessary to have optical access into the systems involved (reactors, etc.) and that is far from being available in most industrial reactors. In addition, scattering cross-sections become very small for powders of nanometric size and the intensity of the scattered light is completely drowned in noise. Consequently, in order to perform measurements that are reliable on powders of nanometric size, it is necessary to seek novel methods that are non-intrusive and that do not require optical access and that do not require samples to be taken.

Numerous businesses are to be found on the market making use of those optical techniques, sometimes in association with systems for charging particles in order to facilitate manipulation thereof. By way of example, those techniques enable particles to be segregated by size. Nevertheless, it is not possible under such circumstances to answer questions associated with the concentration of powders at the places from which they were taken. Among such businesses, mention may be made of some that are very active in this market:

GRIMM (Germany)
MALVERN (Great Britain)
TSI (USA)
NANOSIGHT (Great Britain)
NANEUM (Great Britain)
CILAS (France).

The technologies developed by those businesses make use of light being scattered (or diffracted) by particles in suspension in a liquid solution in which they have previously been immersed. That technique, together with various variants thereof, such as dynamic light scattering, nevertheless presents limits associated with the scattering cross-section when acting on particles in the nanometric range of sizes. With scattering, the scattered intensity is proportional to $r_p^6$ where $r_p$ is the radius of the particles in the powder. Scattering is consequently much more sensitive to the presence of aggregates.

In order to improve performance, another method has been developed by TSI that is based on the mobility of particles. That method, known as scanning mobility particle sizer (SMPS) enables particles to be separated by charge and by electric mobility in order to classify them by size. The particles are initially charged by a corona discharge method.

SMPS technology makes it possible to measure particles in aerosols with concentrations of $10^7$ particles per cubic centimeter ($cm^3$).

In order to make that technique more sensitive to particles in the nanometric size range, Coulter, followed by TSI, make use of the effect of water vapor condensing on the surface of nanoparticles in order to make them more "visible" in laser light scattering. Nevertheless, it is legitimate under such circumstances to ask the following question: is it the "clad" size of the particle that is being measured or its real size?

As a result of research undertaken in the GREMI laboratory over more than fifteen years concerning the formation of nanoparticles in low pressure cold plasmas, it has been shown that it is possible to make use of the modifications in the properties of the discharge induced by the powders to provide detector means. On this topic, reference may be made to the publication by L. Boufendi et al. entitled "Detection of particles of less than 5 nm in diameter formed in an argon-silane capacitively coupled radiofrequency discharge" (Applied Physics Letters—Vol. 79, No. 26—Dec. 24, 2001).

Since then, several research teams in the world have made use of that method in their work. No research work has used that approach for in situ and real time measurement of the size and the concentration of particles of powder that are formed and that remain trapped in levitation in a plasma.

SUMMARY OF THE INVENTION

An object of the present invention is to provide a method that enables the value of the surface radius parameter $r_D$ and/or of the particle density parameter $n_D$ of a nanopowder in levitation in a plasma to be determined by measuring the amplitude of an RF voltage generating the plasma and the value of the self-bias voltage of a first electrode fed with the RF voltage.

The invention thus provides a method of determining the mean surface radius $r_D$ and/or the density $n_D$ of particles of a powder in a sample in levitation in a plasma of volume V formed between a first electrode powered by an RF voltage and a second electrode taken to a constant voltage, in particular ground voltage, the method being characterized in that:

$$n_D = \frac{1}{4\pi K^2 V \Delta A_B} \times \left(\frac{1}{V_{RF}} - \frac{1}{V_{RF(0)}}\right)^{2n}$$

$$r_D = K \frac{\Delta A_B}{\left(\frac{1}{V_{RF}} - \frac{1}{V_{RF(0)}}\right)^n}$$

with:

$$K = \frac{\varepsilon_0 C}{qVD^n}, \Delta A_B = \frac{\frac{\delta(t)}{\delta(0)} - 1}{\frac{1}{A_{M0}} + \frac{1}{A_{B0}}}, \delta(t) \frac{\pi}{\arccos\left(\frac{V_{DC}}{V_{RF}}\right)} - 1$$

and:

$$\delta(0) = \frac{\pi}{\arccos\left(\frac{V_{DC(0)}}{V_{RF(0)}}\right)} - 1$$

$V_{RF}$ designating the amplitude at measurement instant t of the RF voltage feeding the first electrode when the powder is present in the plasma;

$V_{RF(0)}$ designating the amplitude of said RF voltage feeding the first electrode in the absence of powder in the plasma;

$V_{DC}$ designating the self-bias voltage of the first electrode at instant t when the powder is present in the plasma;

$V_{DC(0)}$ designating the self-bias voltage of the first electrode in the absence of powder in the plasma;

$\Delta A_B$ designating the variation in the surface area of the second electrode in the presence of powder at instant t relative to a powder-free situation, $A_{B0}$ and $A_{M0}$ designating the effective surface area of the electrodes in the absence of powder; and the values of n and K being determined by calibration by plotting a curve giving $r_D$ as a function of $\Delta A_B$ and of $V_{RF}$ using experimental data obtained from powders having a known particle diameter by measuring $V_{RF}$, $V_{RF(0)}$, $V_{DC}$ and $V_{DC(0)}$, and by performing regression on said curve, $\alpha$ designating the characteristic discharge surface area with $A_B + A_M = \alpha \Pi$;

$A_B$ and $A_M$ being the characteristic surface areas of the electrodes, and $\alpha = r^2_B + r^2_m$.

The plasma may be an electropositive plasma or an air plasma. The first and second electrodes may form portions of a pre-existing installation, or they may be arranged in a measurement cell provided with suction means.

The invention also provides a device for implementing the method, the device being characterized in that it comprises:
  an RF generator feeding first and second electrodes to generate a said plasma in a volume V extending between said electrodes; and
  a device for measuring the RF voltage $V_{RF}$ and the self-bias voltage $V_{DC}$.

BRIEF DESCRIPTION OF THE DRAWINGS

The invention can be better understood on reading the following description with reference to the accompanying drawings, in which:

FIG. 4 shows the variation over time in the peak-to-peak amplitude $V_{RF}$ of the RF excitation voltage during the formation of a nanopowder;

FIG. 5 shows how the synthesis of a nanopowder is controlled by the self-bias bias ($V_{DC}$) and the magnitude of the discharge current;

DETAILED DESCRIPTION OF THE INVENTION

The terms used in the following description below are listed below.

| Abbreviation | Definition |
|---|---|
| $V_{DC}$ | The self-bias voltage of the electrode B connected to the output of the tuning box (mean value of the electrode potential relative to ground) in the presence of powder, with $V_{DC(0)}$ being the voltage in the absence of powder. |
| $V_{RF}$ | The amplitude at an instant $t$ of the RF voltage feeding the electrode B connected to the output of the tuning box, in the presence of powder, with $V_{RF(0)}$ being the amplitude in the absence of powder. |
| $A_B$ | Effective surface area of electric charge exchange between the plasma and the electrode B connected to the output of the tuning box. |
| $A_M$ | Effective surface area of electric charge exchange between the plasma and the electrode M connected to ground. |
| $\delta(t) = \dfrac{A_B}{A_M}$ | Ratio of the effective surface areas of the electrodes at the instant $t$, where $\delta(0) = \dfrac{A_{B0}}{A_{M0}}$ designates this ratio in the absence of powder. |
| $\alpha$ | Characteristics surface area of the discharge. |
| $\Delta A_B$ | Variation in the effective surface area of electric charge exchange between the plasma and the electrode B connected to the output of the tuning box in the presence of powder within the plasma, relative to a powder-free situation. |
| $\Delta A_M$ | Variation in the effective surface area of electric charge exchange between the plasma and the electrode M connected to ground in the presence of powder within the plasma, relative to a powder-free situation. |
| $r_D$ | Surface radius of particles trapped in the plasma (i.e. the radius of a sphere having the same surface area as a particle of the powder constituting the sample under analysis); this is calculated in the form of a mean using the formula given below. |
| $n_D$ | The particle density or concentration of the powder constituting the sample under analysis within the plasma (expressed in terms of $10^{15}$ particles per $cm^3$). |
| V | Volume occupied by the plasma. |
| $n_i$ | Ion density of the plasma. |
| $n_e$ | Electron density of the plasma. |
| $Z_D$ | Number of elementary charges attached to a partcile of the powder. |
| $T_e$ | Mean electron temperature within the plasma. |
| $\Phi$ | Potential difference between the surface of each particle of the powder and the plasma. |
| $\epsilon_0$ | Permittivity of vacuum ($8.85 \times 10^{-12}$ farads per meter (F/m)). |
| q | Elementary electric charge ($1.6 \times 10^{-19}$ coulombs (C)). |

The invention applies more particularly to a cold plasma (i.e. $kT_e \leq 10$ electron volts (eV), where k is Boltzman's constant) at low pressure (i.e. at a pressure P<1 millibar (mbar)).

The plasma may equally well be an electropositive plasma (e.g. an argon plasma) or an air plasma, since the measurement method is differential, as can be seen from the description below.

Figure 1:
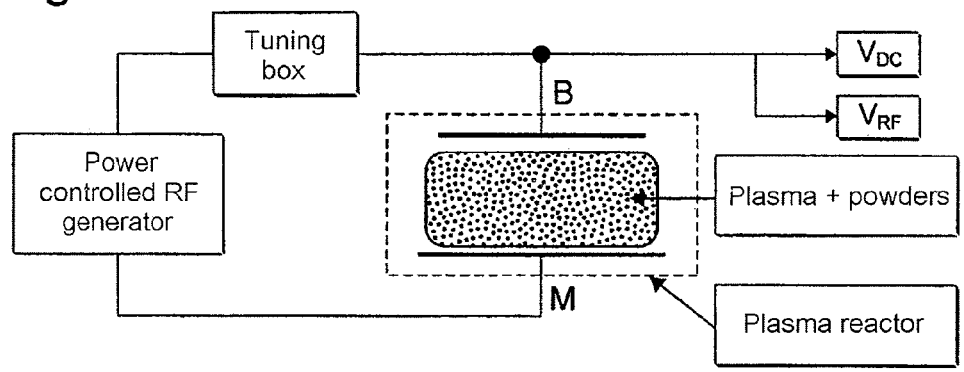
FIG. 1 is a diagram of a device for implementing the invention.

According to the invention, and with reference to FIG. 1, the plasma is initiated in a plasma reactor by means of an RF capacitive discharge that is servo-controlled in power. Capacitive coupling with an RF generator for delivering an RF excitation voltage of amplitude $V_{RF}$ is obtained by an L tuning box that is known in itself. When the plasma is established between the electrodes, there naturally appears a self-bias voltage $V_{DC}$ at the electrode B that receives the excitation voltage. The electrode M is generally connected to ground.

Figure 2:
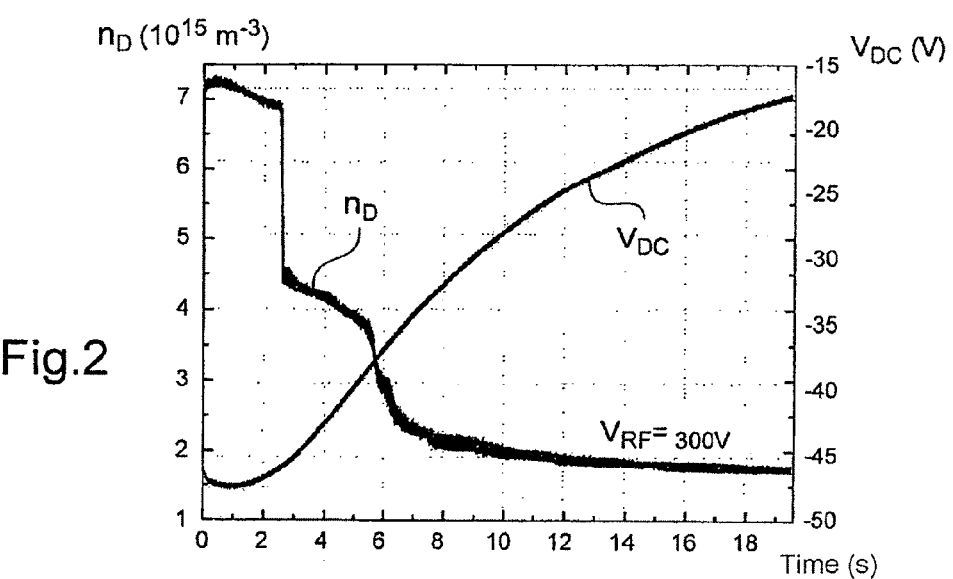
FIGS. 2 and 3 show how the self-bias voltage and the electron density vary during the growth of a nanopowder in a low-pressure cold plasma (FIG. 2) and the correlation thereof with the amplitude of the third harmonic of the discharge current (FIG. 3)
Figure 3:
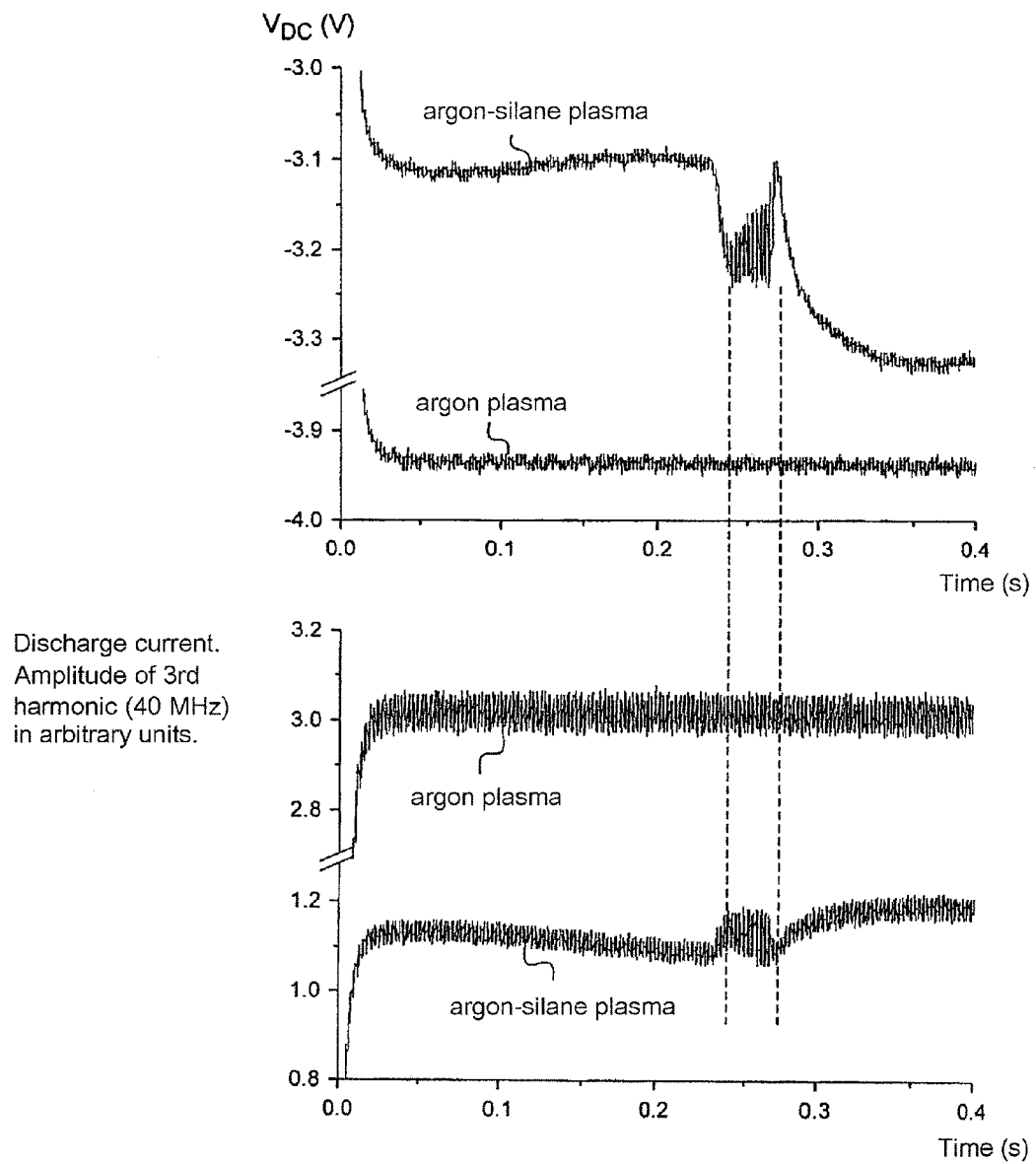

When the powder particles appear in the plasma (by growing or indeed by being injected), the characteristics of the plasma change. Amongst these changes, there can be observed a drop in electron density, a rise in electron temperature, and variation in $V_{DC}$ (FIGS. 2 and 3) and in $V_{RF}$ (FIG. 4).

This method of detecting powders at different stages in their growth has been validated by depositing nanopowders on a substrate of silica ($SiO_2$). That involves powder nucleation and growth in a gas in a plasma. The nucleation and growth result from conventional reactions that involve reactive species, radicals (fragments of molecules) that are produced by dissociating reactive molecules such as silane or methane, etc. . . . , by the products of plasma etching, e.g. $SiF_x$ (where x=1, 2, or 3), or indeed the products of plasma sputtering.

These mechanisms have been studied and are summarized in the following publication: André Bouchoule et al. in Pure and Appl. Chem., Vol. 68, No. 5, pp. 1121-1126 (1996).

FIG. 5 shows that it is possible to control powder synthesis before and after starting a nanocrystallite agglomeration stage at time $t_2$.

These curves show the presence of solid particles within the plasma. Furthermore, studying the cross-correlation between the effects that are obtained has made it possible to develop a method of measuring the particle size and/or the particle density of a single-sized (or mono-dispersed) sample trapped within the plasma. This method is relatively simple, since it enables the sample to be analyzed from a measurement of the modifications in the excitation voltage and the self-bias voltage $V_{DC}$ as induced by the appearance of powder within the plasma.

It is specified at this point that the value of $V_{RF}$ that is taken into account is the amplitude of the RF excitation voltage proper, and that the value of $V_{DC}$ that is taken into account is the mean value of the potential of the electrode B relative to ground.

Measurement Range:

Size: determining the mean surface radius $r_D$ of particles or agglomerates of a powder in a range extending from a diameter of a few nanometers to several micrometers (e.g. 2 nm to 10 μm).

Particle density: the range of particle densities depends on the size of the particles of the powder constituting the sample. From experiments, in which $V_{DC}$ can be measured with an accuracy of 10 millivolts (mV), the smallest mass of a carbon powder particle that can be analyzed is less than 1 microgram (μg). This threshold corresponds to $10^8$ particles per $cm^3$ for particles having a radius of 10 nm or to $10^5$ particles per $cm^3$ for particles having a radius of 1 μm. It is possible to lower this threshold by using measurement electronics that are more sensitive, since the figures given above were obtained using a minimum detectable variation in $V_{DC}$ of 10 mV.

Demonstration of the Method

From the publication by E. Kawamura [E. Kawamura, V. Vahedi, M. A. Lieberman, and C. K. Birdsall, entitled "Ion energy distributions in RF sheaths; review, analysis, and simulation" published in "Plasma Source Sci. Technol. 8, R45-R64, 1999", IOP Publishing Ltd] that relate solely to a conventional plasma, i.e. a plasma that does not contain powder particles, the following applies at an instant t:

$$V_{DC} = V_{RF}\cos\left(\frac{\pi}{1+\delta}\right) \quad \text{Eq. 1}$$

$$\text{i.e. } \delta = \frac{A_B}{A_M} = \frac{\pi}{\arccos\left(\frac{V_{DC}}{V_{RF}}\right)} - 1 \quad \text{Eq. 2}$$

Thus, the effective surface areas of charge exchange between the plasma and the electrodes may be expressed as follows:

$$A_B = \alpha\left(\pi - \arccos\left(\frac{V_{DC}}{V_{RF}}\right)\right) \quad \text{Eq. 3}$$

$$A_M = \alpha\left(\arccos\left(\frac{V_{DC}}{V_{RF}}\right)\right) \quad \text{Eq. 4}$$

where $\alpha$ is the characteristic surface area of the discharge.

Consequently, it can be seen that:

$$\frac{dA_B}{d\left(\frac{V_{DC}}{V_{RF}}\right)} = \frac{\alpha}{\sqrt{1-\left(\frac{V_{DC}}{V_{RF}}\right)^2}} = -\frac{dA_M}{d\left(\frac{V_{DC}}{V_{RF}}\right)} \text{ whence} \quad \text{Eq. 5}$$

$$\Delta A_B = -\Delta A_M$$

In other words, the variation in the effective surface area of charge exchange between the plasma and one of the two electrodes is compensated by the variation in the surface area of charge exchange between the plasma and the other electrode.

At this point, in the context of the present invention, consideration is given to $\delta_0$ and $\delta_1$ as being respectively the ratio $$\frac{A_{B0}}{A_{M0}}$$

in the absence of powder and the ratio $$\frac{A_B}{A_M}$$

in the presence of powder and with:

$$A_B = A_{B0} \Delta A_B \text{ and } A_M = A_{M0} + \Delta A_M$$

This gives:

$$\delta_1 = \frac{A_{B0} + \Delta A_B}{A_{M0} - \Delta A_B} = \delta_0 \times \frac{1+\frac{\Delta A_B}{A_{B0}}}{1-\frac{\Delta A_B}{A_{M0}}} \quad \text{Eq. 6}$$

The variation in the surface area of the electrode B is associated with the cumulative surface area of the powders trapped in the plasma. Thus:

$$\Delta A_B \approx 4\pi V \int_{r_{min}}^{r_{max}} r_D^2 n_D(r_D)\, dr_D \quad \text{Eq. 7}$$

where $r_{min}$ and $r_{max}$ designate the minimum and maximum values of the radius $r_D$ of the particles present in the powder.

Figure 6:
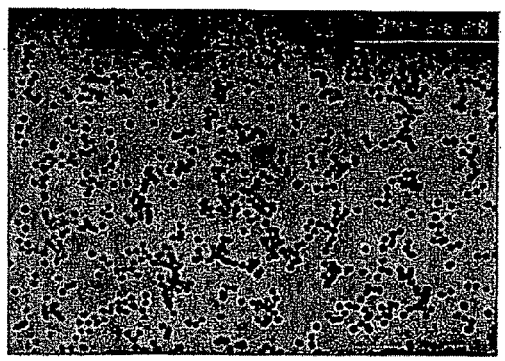
FIG. 6 is a photograph of nanoparticles of a nanopowder formed in a plasma.

With a sample that is monodispersed comprising spherical particles all having the same size (as shown in FIG. 6), the following applies:

$$\Delta A_B = 4\pi V r_D^2 n_D \quad \text{Eq. 8}$$

Furthermore, the presence of particles within the plasma modifies the expression for the plasma being almost electrically neutral. Consequently the following applies:

$$n_i = n_e + Z_D n_D \quad \text{Eq. 9}$$

By considering the particles or agglomerates of powder immersed in the plasma as being spherical capacitors having one plate at a floating potential (the potential at the surface of a particle), and the other plate at the potential of the plasma, the number $Z_D$ of electrons attached to each particle of the powder may be expressed as a function of the radius of the particle and of the (mean) difference of the potential $|\Phi|$ between the plasma and each particle of powder (Gauss' theorem):

$$Z_D = \frac{4\pi\varepsilon_0}{q} r_D |\Phi| \quad \text{Eq. 10}$$

From the above two equations, it is possible to express the "size×density" product of the sample:

$$r_D n_D = \frac{q(n_i - n_e)}{4\pi\varepsilon_0 |\Phi|} \quad \text{Eq. 11}$$

By associating equations 8 and 11, the following are obtained:

$$n_D = \frac{q(n_i - n_e)}{4\pi\varepsilon_0 |\Phi| r_D} \quad \text{Eq. 12}$$

$$r_D = \frac{\Delta A_B \varepsilon_0 |\Phi|}{q(n_i - n_e) \times V} \quad \text{Eq. 13}$$

These equations provide a method that makes it possible to determine the mean surface radius $r_D$ and the particle density $n_D$ of a sample of powders trapped in the plasma. Nevertheless, it is quite difficult to implement that method since it requires knowledge of the electron and ion densities and also of the mean electron temperature, which parameter has a great influence on determining $|\Phi|$.

These parameters vary during the growth of silicon or carbon nanopowders in low-pressure cold plasmas.

From these measurements, and as can be seen from the curve below, the following applies:

$$\frac{|\Phi|}{n_i - n_e} = \frac{C}{(T_e - T_e(0))^n} \quad \text{Eq. 14}$$

With $T_e(0)$ being the electron temperature of the plasma without any powder, and $T_e$ being the electron temperature at the instant t in the presence of powder.

Figure 7:
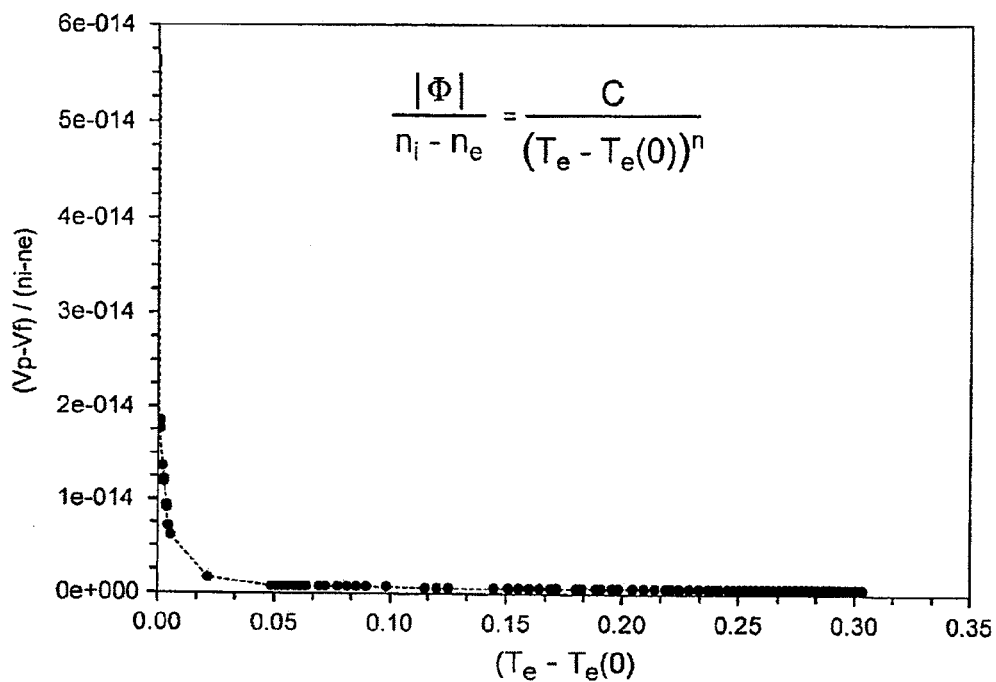
FIG. 7 shows the relationship between $\Phi$, $n_i - n_e$, and the variation in electron temperature in the presence of powder particles or agglomerates of powder particles.

FIG. 7 shows the relationship between $|\Phi|$, $n_i-n_e$ and the variation in the electron temperature in the presence of powder.

Figure 8A:
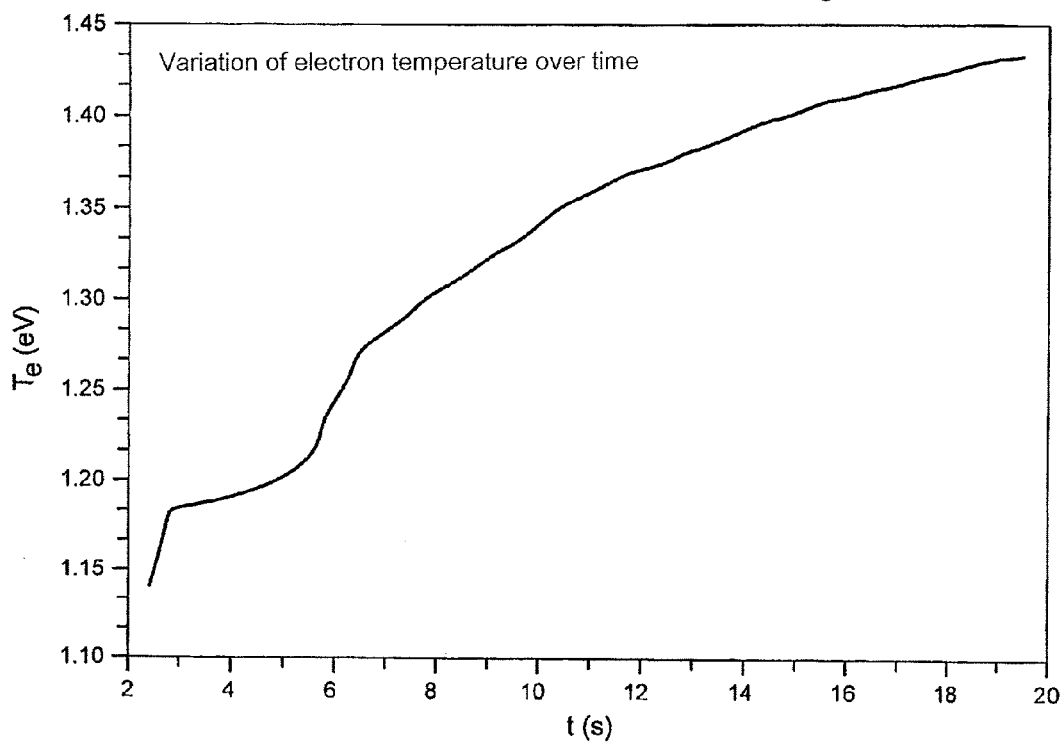
FIGS. 8a to 8c show the relationship $V_{RF} \times T_e =$ constant during the growth of a nanopowder.
Figure 8B:
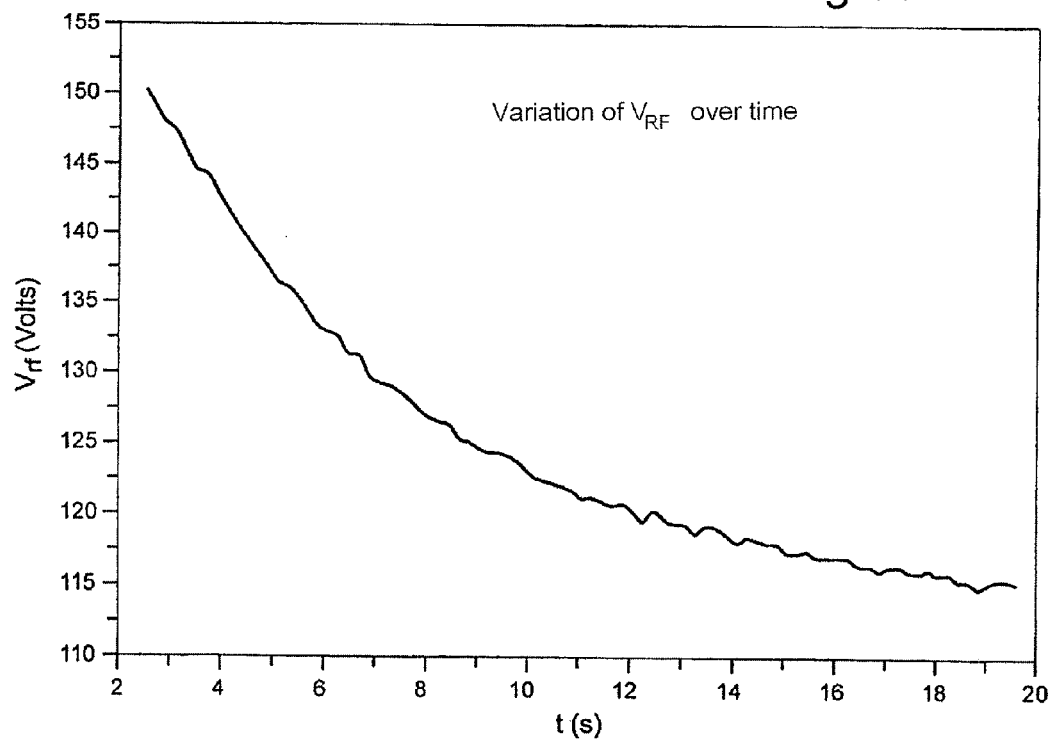
Figure 8C:
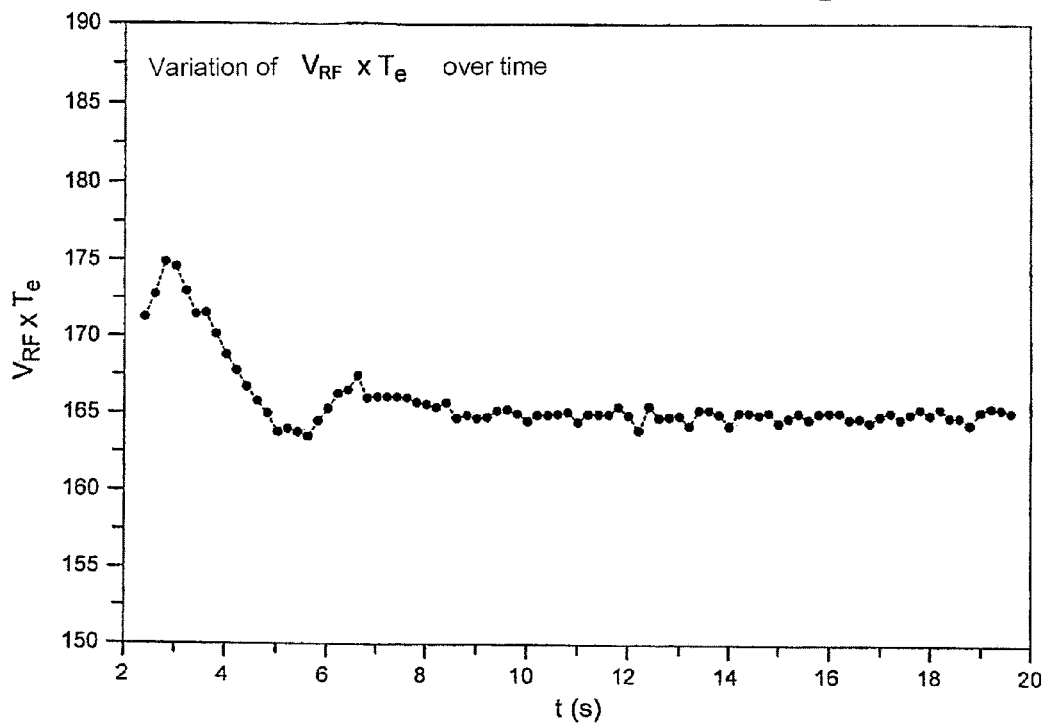

Furthermore, as can be seen in FIGS. 8a to 8c in which FIGS. 8a and 8b show the variation respectively in $T_e$ and $V_{RF}$, and FIG. 8c shows the product $V_{RF} \times T_e$, and because of the power servo-control of the RF generator, the following applies:

$$V_{RF} \times Te = \text{Const}$$

during the growth of nanopowders, where $T_e$ designates the electron temperature at instant t and $T_e(0)$ designates the electron temperature in the absence of powder (instant 0).

The following thus applies:

$$T_e - T_e(0) = D\left(\frac{1}{V_{RF}} - \frac{1}{V_{RF}(0)}\right) \quad \text{Eq. 15}$$

with D=Const

Finally, the following applies:

$$n_D = \frac{q^2}{4\pi\varepsilon_0^2} \frac{D^{2n}\left(\frac{1}{V_{RF}} - \frac{1}{V_{RF}(0)}\right)^{2n}}{C^2} \frac{V}{\Delta A_B} = \frac{1}{4\pi K^2 V \Delta A_B} \times \left(\frac{1}{V_{RF}} - \frac{1}{V_{RF}(0)}\right)^{2n} \quad \text{Eq. 16}$$

$$r_D = \frac{\Delta A_B}{V} \frac{\varepsilon_0}{q} \frac{C}{D^n\left(\frac{1}{V_{RF}} - \frac{1}{V_{RF}(0)}\right)^n} = K \frac{\Delta A_B}{\left(\frac{1}{V_{RF}} - \frac{1}{V_{RF}(0)}\right)^n} \quad \text{Eq. 17}$$

with $$K = \frac{\varepsilon_0 C}{qVD^n}, \Delta A_B(t) = \frac{\frac{\delta(t)}{\delta(0)} - 1}{\frac{1}{A_{M0}} + \frac{1}{A_{B0}}} \text{ and } \delta(t) = \frac{\pi}{\arccos\left(\frac{V_{DC}}{V_{RF}}\right)} - 1$$

where $V_{DC}$ and $V_{RF}$ designates the value of the self-bias voltage and of the excitation voltage at instant $t_0$, while $V_{DC(0)}$ and $V_{RF(0)}$ express the same two values in the absence of powder (instant zero).

Thus, there are two constants to be calibrated: n and K. This may be done by analyzing various calibrated samples of powder made up of particles of known diameter. It can also be observed that the uncertainty concerning particle density is associated with the estimated volume V of the plasma.

Calibration:

In an $Ar+CH_4$ plasma, carbon nanopowder particles are grown having a particle size that is known, of value $r_D$ that is known and lies in the range 10 nm to 100 nm in diameter, or else powders are used having particles of known diameter. With knowledge of $V_{RF}(r_D)$ and $V_{DC}(r_D)$ it is possible to plot $$r_D = f(\Delta A_B, \Delta V_{RF}^{-1}) = \Delta A_B/(1/V_{RF} - 1/V_{RF(0)})$$

Thereafter, using linear regression, it is possible to determine n and K. This linear regression gives calculated values for $r_D$ that are written $r_{D\text{-}fit}$.

The following are found:

$$K = 6.4 \times 10^{-6} \text{ and } n = 0.307 \text{ and}$$

$$r_{D\text{-}fit} = K \frac{\Delta A_B}{\left(\frac{1}{V_{RF}} - \frac{1}{V_{RF}(0)}\right)^n}$$

Figure 9:
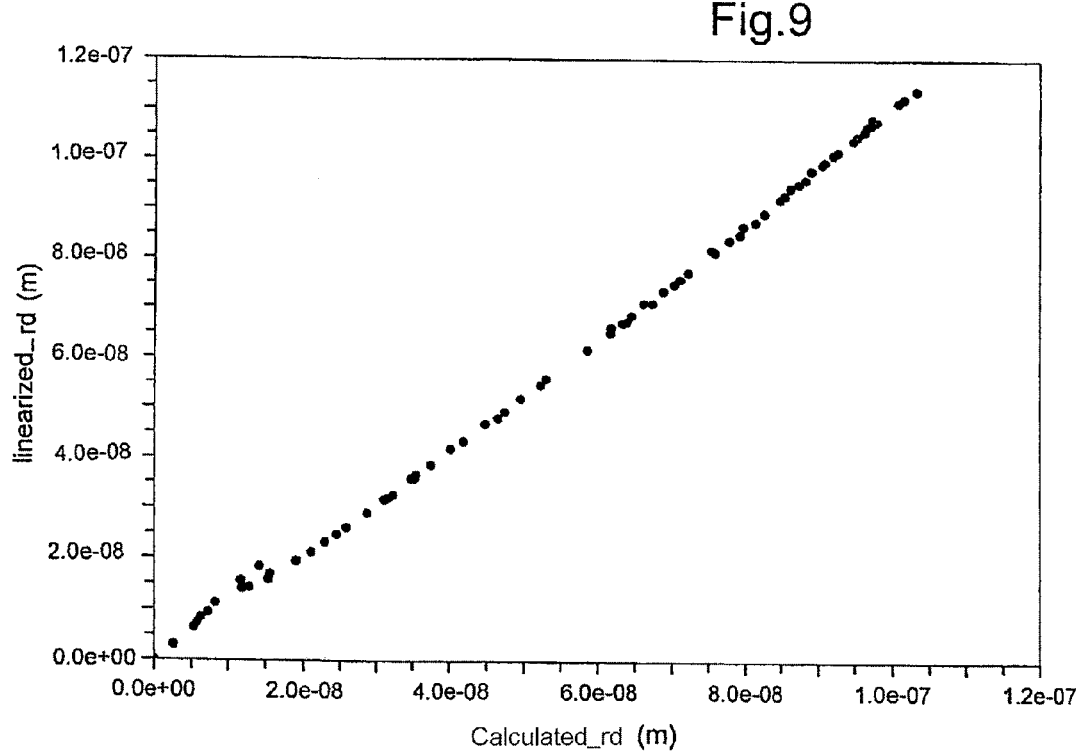
FIG. 9 shows the relationship between known linearized $r_D$ and calculated $r_D$ as determined in this way by calculation, expressed in meters.

To verify the relationship, it is possible to plot $r_D = f(r_{D\text{-}fit})$ i.e. the relationship between the known value $r_D$ and the value as calculated by the invention, in order to observe that there is indeed a linear relationship between the radius as calculated by the method and the linearized radius as obtained from $V_{DC}$ (see FIG. 9), thereby validating the values for n and K that can be used for determining $r_D$ and/or $n_D$ for a powder that is introduced between the electrodes and that has parameters that are not known.

Figure 10:
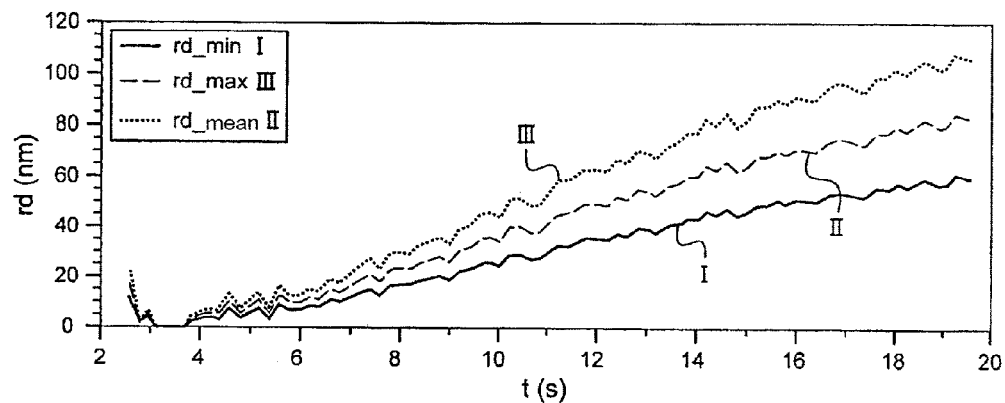
FIGS. 10 and 11 show the relationship between the radius (in nanometers (nm)) of known powders $r_D$ as determined by calculation, and the particle density as measured directly and estimated by calculation.
Figure 11:
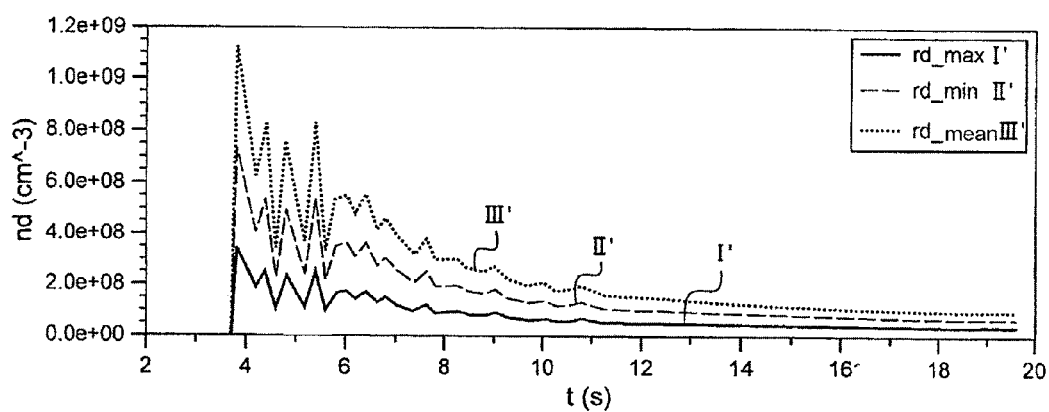

FIGS. 10 and 11 show the simultaneous variation in the radius $r_D$ and the particle density $n_D$ of a powder during a growth period of 20 seconds (s) during which agglomerates are formed.

The method of the invention enables such curves to be plotted from the instantaneous values of the voltages $V_{RF}$ and $V_{DC}$ as measured starting from the initial instant (before introducing the powder).

$r_D$ depends on K, on n, and on the excitation voltage and on $\Delta A_B$. K and n are determined by calibration and $\Delta A_B$ depends on the voltages $V_{DC}$ and $V_{RF}$.

$n_D$ also depends on the volume V of the plasma and its value is estimated as being substantially equal to the volume that is available between the two electrodes.

Figure 12:
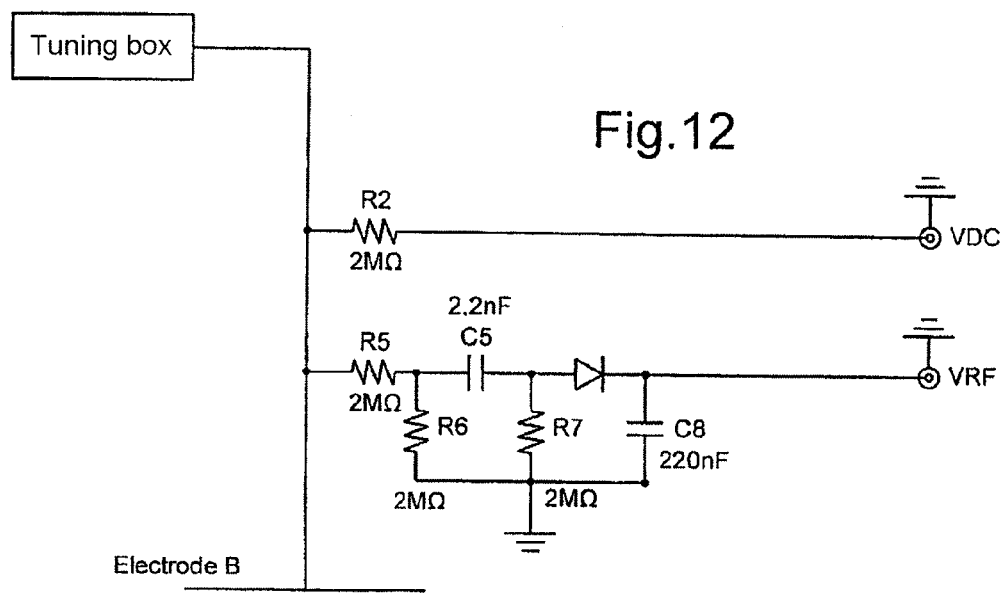
FIG. 12 shows a preferred embodiment of a device for measuring radiofrequency voltages $V_{RF}$ and/or self-bias voltages $V_{DC}$.

FIG. 12 shows an embodiment of a circuit for measuring the potential $V_{RF}$ and the self-bias potential $V_{DC}$, which circuit is connected to the electrode B at the output from the tuning box. This circuit is designed to present very high impedance (in practice >500 kilohms (kΩ) or preferably >1 megohm (MΩ)) so as to avoid disturbing the formation of the plasma. It is suitable for connection to any existing device optionally including an incorporated measurement device. The measurement devices presently in use in industrial installations lack accuracy, and are generally not suitable for the method of the invention.

Measuring $V_{DC}$: the self-bias voltage is measured with a resistor capacitor (RC) type lowpass filter. The capacitor is not shown in the diagram since it is constituted by the stray capacitance of the BNC type coaxial cable (≈30 picofarads (pF)) used for connecting the output $V_{DC}$ to an oscilloscope or to a voltage measuring device.

Measuring $V_{RF}$: the amplitude of the voltage applied to the electrode B is measured with a peak detector using a fast diode of the Schottky type coupled to a measurement capacitor C8. A highpass filter (R7, C5) is arranged ahead of the diode in order to eliminate the direct current (DC) component of the signal. A voltage divider bridge (R5, R6) that may be arranged ahead of the filter serves to protect the diode from overvoltages.

Furthermore, it is important for these two measurement circuits to present high input impedance in order to avoid disturbing the potential of the electrode B. It is also necessary to take care to select a high input impedance (1 MΩ) for the oscilloscope channels connected to the circuit.

The measurement circuit may be associated with a module for calculating the surface radius $r_D$ and/or the particle density $n_D$, in accordance with the above equations.

The method of the invention may be applied to the appearance and to the growth of nanopowders in a low pressure plasma and also to nanopowders that are injected or sucked in. The invention applies in particular:

- to monitoring the particle contamination of plasma reactors used in microelectronics: the device may thus be used for a sealed device, it being possible for a detector to be arranged in situ inside the plasma reactor;
- to monitoring white rooms in which reactors and other pieces of equipment are installed, thus enabling personnel to be protected. For this purpose, the powder is sucked in so that it comes between the electrode, and the plasma is obtained in air; and
- to monitoring the environment in laboratories or workshops, with a plasma being formed in air.

The invention claimed is:

1. A method of determining the mean surface radius $r_D$ or the density $n_D$ of particles of a powder in a sample in levitation in a plasma of volume V formed between a first electrode powered by an RF voltage and a second electrode taken to a ground voltage, the method being characterized in that:

$$n_D = \frac{1}{4\pi K^2 V \Delta A_B} \times \left(\frac{1}{V_{RF}} - \frac{1}{V_{RF(0)}}\right)^{2n}$$

$$r_D = K \frac{\Delta A_B}{\left(\frac{1}{V_{RF}} - \frac{1}{V_{RF(0)}}\right)^n}$$

with:

$$K = \frac{\varepsilon_0 C}{qVD^n},\ \Delta A_B = \frac{\frac{\delta(t)}{\delta(0)} - 1}{\frac{1}{A_{M0}} + \frac{1}{A_{B0}}},\ \delta(t) = \frac{\pi}{\arccos\left(\frac{V_{DC}}{V_{RF}}\right)} - 1$$

and:

$$\delta(0) = \frac{\pi}{\arccos\left(\frac{V_{DC(0)}}{V_{RF(0)}}\right)} - 1$$

$V_{RF}$ designating the amplitude at measurement instant t of the RF voltage feeding the first electrode when the powder is present in the plasma;

$V_{RF(0)}$ designating the amplitude of said RF voltage feeding the first electrode in the absence of powder in the plasma;

$V_{DC}$ designating the self-bias voltage of the first electrode at instant t when the powder is present in the plasma;

$V_{DC(0)}$ designating the self-bias voltage of the first electrode in the absence of powder in the plasma;

$\Delta A_B$ designating the variation in the surface area of the second electrode in the presence of powder at instant t relative to a powder-free situation, $A_{B0}$ and $A_{M0}$ designating the effective surface area of the electrodes in the absence of powder; and the values of n and K being determined by calibration by plotting a curve giving $r_D$ as a function of $\Delta A_B$ and of $V_{RF}$ using experimental data obtained from powders having a known particle diameter by measuring $V_{RF}$, $V_{RF(0)}$, $V_{DC}$, and $V_{DC(0)}$, and by performing regression on said curve.

2. A method according to claim 1, wherein the plasma is an electropositive plasma.

3. A method according to claim 1, wherein the plasma is an air plasma.

4. A method according to claim 3, wherein that the first and second electrodes are arranged in a cell provided with suction means.

5. A device for implementing the method of claim 1, the device comprising:

an RF generator feeding first and second electrodes to generate a said plasma in a volume V extending between said electrodes; and a device for measuring the RF voltage $V_{RF}$ and the self-bias voltage $V_{DC}$.

6. A device according to claim 5, wherein the device for measuring the RF voltage $V_{RF}$ includes a highpass filter (R7, C5) arranged upstream from a Schottky diode that forms a peak detector.

7. A device according to claim 6, wherein the device includes a divider bridge (R5, R6) upstream from the highpass filter.

8. A device according to claim 5, wherein the device for measuring the self-bias voltage $V_{DC}$ includes a lowpass filter.

9. A device according to claim 8, wherein the lowpass filter presents a resistor (R2) and a capacitor constituted by the capacitance of a cable in series with said resistor (R2).

10. A device according to claim 5, wherein the device includes a model for calculating the surface radius $r_D$ and/or the particle density $n_D$ in accordance with the following equations $$n_D = \frac{1}{4\pi K^2 V \Delta A_B} \times \left(\frac{1}{V_{RF}} - \frac{1}{V_{RF(0)}}\right)^{2n}$$

$$r_D = K \frac{\Delta A_B}{\left(\frac{1}{V_{RF}} - \frac{1}{V_{RF(0)}}\right)^n}$$

with:

$$K = \frac{\varepsilon_0 C}{qVD^n},\ \Delta A_B = \frac{\frac{\delta(t)}{\delta(0)} - 1}{\frac{1}{A_{M0}} + \frac{1}{A_{B0}}},\ \delta(t) = \frac{\pi}{\arccos\left(\frac{V_{DC}}{V_{RF}}\right)} - 1$$

and:

$$\delta(0) = \frac{\pi}{\arccos\left(\frac{V_{DC(0)}}{V_{RF(0)}}\right)} - 1$$

$V_{RF}$ designating the amplitude at measurement instant t of the RF voltage feeding the first electrode when the powder is present in the plasma;

$V_{RF(0)}$ designating the amplitude of said RF voltage feeding the first electrode in the absence of powder in the plasma;

$V_{DC}$ designating the self-bias voltage of the first electrode at instant t when the powder is present in the plasma;

$V_{DC(0)}$ designating the self-bias voltage of the first electrode in the absence of powder in the plasma;

$\Delta A_B$ designating the variation in the surface area of the second electrode in the presence of powder at instant t relative to a powder-free situation, $A_{B0}$ and $A_{M0}$ designating the effective surface area of the electrodes in the absence of powder; and the values of n and K being determined by calibration by plotting a curve giving $r_D$ as a function of $\Delta A_B$ and of $V_{RF}$ using experimental data obtained from powders having a known particle diameter by measuring: $V_{RF}$, $V_{RF(0)}$, $V_{DC}$, and $V_{DC(0)}$, and by performing regression on said curve.

* * * * *